(12) United States Patent
Bickel et al.

(10) Patent No.: US 10,403,404 B2
(45) Date of Patent: Sep. 3, 2019

(54) PHYSICAL FACE CLONING

(71) Applicant: Disney Enterprises, Inc., Burbank, CA (US)

(72) Inventors: Bernd Bickel, Zurich (CH); Peter Kaufmann, Liebefeld (CH); Bernhard Thomaszewski, Zurich (CH); Derek Edward Bradley, Zurich (CH); Philip John Jackson, Glendale, CA (US); Stephen R. Marschner, Ithaca, NY (US); Wojciech Matusik, Lexington, MA (US); Markus Gross, Uster (CH); Thabo Dominik Beeler, Savognin (CH)

(73) Assignees: Disney Enterprises, Inc., Burbank, CA (US); ETH Zurich (Eidgenoessiche Technische Hochschule Zurich), Zurich (CH)

( * ) Notice: Subject to any disclaimer, the term of this patent is extended or adjusted under 35 U.S.C. 154(b) by 504 days.

(21) Appl. No.: 14/797,755

(22) Filed: Jul. 13, 2015

(65) Prior Publication Data

US 2015/0317451 A1    Nov. 5, 2015

Related U.S. Application Data

(63) Continuation of application No. 13/275,481, filed on Oct. 18, 2011, now Pat. No. 9,082,222.

(Continued)

(51) Int. Cl.
G06T 19/20     (2011.01)
G16H 50/50    (2018.01)
(Continued)

(52) U.S. Cl.
CPC .............. *G16H 50/50* (2018.01); *G06F 17/10* (2013.01); *G06T 19/20* (2013.01); *A61B 5/442* (2013.01);

(Continued)

(58) Field of Classification Search
None
See application file for complete search history.

(56) References Cited

U.S. PATENT DOCUMENTS

| 5,159,362 A | 10/1992 | Monroe et al. |
| 6,044,168 A | 3/2000 | Tuceryan et al. |

(Continued)

OTHER PUBLICATIONS

U.S. Appl. 61/433,923, entitled "Physical Face Cloning", filed Jan. 18, 2011.

(Continued)

*Primary Examiner* — Kibrom K Gebresilassie
(74) *Attorney, Agent, or Firm* — Patterson + Sheridan, LLP

(57) ABSTRACT

A computer-implemented method is provided for physical face cloning to generate a synthetic skin. Rather than attempt to reproduce the mechanical properties of biological tissue, an output-oriented approach is utilized that models the synthetic skin as an elastic material with isotropic and homogeneous properties (e.g., silicone rubber). The method includes capturing a plurality of expressive poses from a human subject and generating a computational model based on one or more material parameters of a material. In one embodiment, the computational model is a compressible neo-Hookean material model configured to simulate deformation behavior of the synthetic skin. The method further includes optimizing a shape geometry of the synthetic skin based on the computational model and the captured expressive poses. An optimization process is provided that varies the thickness of the synthetic skin based on a minimization of an elastic energy with respect to rest state positions of the synthetic skin.

20 Claims, 7 Drawing Sheets

Related U.S. Application Data

(60) Provisional application No. 61/433,923, filed on Jan. 18, 2011.

(51) Int. Cl.
  *G06F 17/10* (2006.01)
  *G06K 9/00* (2006.01)
  *G06T 17/00* (2006.01)
  *A61B 5/00* (2006.01)
  *G10L 21/10* (2013.01)
  *G06T 17/10* (2006.01)
  *G06F 17/50* (2006.01)

(52) U.S. Cl.
  CPC .. *A63F 2300/6607* (2013.01); *G06F 17/5018* (2013.01); *G06K 9/00268* (2013.01); *G06T 17/00* (2013.01); *G06T 17/10* (2013.01); *G06T 2207/30201* (2013.01); *G06T 2219/2021* (2013.01); *G10L 2021/105* (2013.01)

(56) References Cited

U.S. PATENT DOCUMENTS

| | | | |
|---|---|---|---|
| 6,064,390 A | 5/2000 | Sagar et al. | |
| 6,072,496 A | 6/2000 | Guenter et al. | |
| 6,300,960 B1 | 10/2001 | DeRose et al. | |
| 6,492,990 B1 | 12/2002 | Peleg et al. | |
| 6,664,956 B1 | 12/2003 | Erdem | |
| 6,876,364 B2 | 4/2005 | Buddemeier et al. | |
| 6,944,320 B2 | 9/2005 | Liu et al. | |
| 7,113,848 B2 | 9/2006 | Hanson | |
| 7,164,718 B2 | 1/2007 | Maziere et al. | |
| 7,202,869 B2* | 4/2007 | Tooley | G06T 13/40 345/473 |
| 7,209,577 B2 | 4/2007 | McAlpine et al. | |
| 7,212,656 B2 | 5/2007 | Liu et al. | |
| 7,239,321 B2* | 7/2007 | Berger | G06T 13/40 345/473 |
| 7,515,155 B2* | 4/2009 | Anderson | G06T 13/40 345/473 |
| 7,548,236 B2* | 6/2009 | Ikezawa | G06T 15/04 345/419 |
| 8,050,512 B2 | 11/2011 | Daly et al. | |
| 8,139,068 B2* | 3/2012 | Isner | G06T 13/40 345/419 |
| 8,144,153 B1* | 3/2012 | Sullivan | G06T 13/40 345/473 |
| 8,207,971 B1 | 6/2012 | Koperwas et al. | |
| 8,334,872 B2 | 12/2012 | Epps et al. | |
| 8,358,311 B1* | 1/2013 | Witkin | G06T 19/00 345/474 |
| 8,456,476 B1* | 6/2013 | Kovar | G06T 13/40 345/474 |
| 8,472,700 B2 | 6/2013 | Kim et al. | |
| 8,542,236 B2 | 9/2013 | Sullivan et al. | |
| 8,568,642 B2 | 10/2013 | Jackson et al. | |
| 8,581,911 B2* | 11/2013 | Becker | G06T 13/40 345/418 |
| 8,594,839 B2 | 11/2013 | Hanson | |
| 8,681,158 B1* | 3/2014 | Sullivan | G06T 17/20 345/419 |
| 8,847,963 B1* | 9/2014 | Comet | G06T 19/20 345/419 |
| 8,917,317 B1 | 12/2014 | Beeler | |
| 9,082,222 B2* | 7/2015 | Bickel | G06T 19/20 |
| 9,317,955 B1* | 4/2016 | Jensen | G06T 13/80 |
| 2003/0088389 A1 | 5/2003 | Balaniuk et al. | |
| 2003/0097691 A1* | 5/2003 | Potter | C12Q 1/6895 800/295 |
| 2003/0110540 A1 | 6/2003 | Fukui et al. | |
| 2003/0160791 A1* | 8/2003 | Breton | G06T 13/40 345/473 |
| 2004/0095352 A1* | 5/2004 | Huang | G06T 13/40 345/473 |
| 2004/0254771 A1 | 12/2004 | Riener et al. | |
| 2004/0257368 A1* | 12/2004 | Anderson | G06T 13/40 345/473 |
| 2005/0057569 A1* | 3/2005 | Berger | G06T 13/40 345/473 |
| 2005/0078124 A1 | 4/2005 | Liu et al. | |
| 2005/0213820 A1 | 9/2005 | Liu et al. | |
| 2005/0256686 A1 | 11/2005 | Stabelfeldt et al. | |
| 2006/0015308 A1 | 1/2006 | Marschner et al. | |
| 2006/0104491 A1 | 5/2006 | Liu et al. | |
| 2006/0126924 A1 | 6/2006 | Liu et al. | |
| 2006/0164440 A1* | 7/2006 | Sullivan | G06T 19/20 345/639 |
| 2006/0192785 A1 | 8/2006 | Marschner et al. | |
| 2007/0229498 A1* | 10/2007 | Matusik | G06T 17/20 345/420 |
| 2008/0100622 A1* | 5/2008 | Gordon | H04N 5/228 345/427 |
| 2008/0170078 A1* | 7/2008 | Sullivan | G06T 17/20 345/473 |
| 2008/0170777 A1 | 7/2008 | Sullivan et al. | |
| 2008/0180448 A1 | 7/2008 | Anguelov et al. | |
| 2008/0231640 A1 | 9/2008 | Pighin et al. | |
| 2009/0028380 A1 | 1/2009 | Hillebrand et al. | |
| 2009/0135189 A1 | 5/2009 | Kim et al. | |
| 2009/0289391 A1 | 11/2009 | Tye et al. | |
| 2010/0007665 A1 | 1/2010 | Smith et al. | |
| 2010/0049451 A1* | 2/2010 | Lu | G01N 3/12 702/42 |
| 2010/0076306 A1 | 3/2010 | Daigneault et al. | |
| 2010/0222914 A1* | 9/2010 | Tye | A63H 9/00 700/118 |
| 2011/0066239 A1 | 3/2011 | Smoot et al. | |
| 2011/0087354 A1* | 4/2011 | Tye | A63H 9/00 700/98 |
| 2011/0115798 A1* | 5/2011 | Nayar | G06T 13/40 345/473 |
| 2011/0141115 A1 | 6/2011 | Brandes et al. | |
| 2011/0304622 A1 | 12/2011 | Rogers et al. | |
| 2012/0007859 A1 | 1/2012 | Lee et al. | |
| 2012/0038739 A1 | 2/2012 | Welch et al. | |
| 2012/0053716 A1* | 3/2012 | Bickel | B29C 67/0088 700/98 |
| 2012/0139830 A1 | 6/2012 | Hwang et al. | |
| 2012/0156419 A1* | 6/2012 | Jackson | B29C 39/10 428/99 |
| 2012/0185218 A1* | 7/2012 | Bickel | G06T 19/20 703/1 |
| 2012/0313937 A1 | 12/2012 | Beeler et al. | |
| 2012/0327194 A1 | 12/2012 | Shiratori et al. | |
| 2013/0002669 A1 | 1/2013 | Rhee et al. | |
| 2013/0070094 A1 | 3/2013 | Majumder et al. | |
| 2013/0121526 A1* | 5/2013 | Smolyanskiy | G06T 17/00 382/103 |
| 2013/0235045 A1 | 9/2013 | Corazza et al. | |
| 2013/0271485 A1* | 10/2013 | Aoki | A45D 44/005 345/593 |
| 2013/0307848 A1 | 11/2013 | Tena et al. | |
| 2014/0085293 A1* | 3/2014 | Konoplev | A63F 13/12 345/419 |

OTHER PUBLICATIONS

Becker, Markus et al., Robust and Efficient Estimation of Elasticity Parameters using the Linear Finite Element Method, SimVis GmbH, 2007, pp. 15-28, Vienna, Austria.

Beeler, T. et al., High-quality single-shot capture of facial geometry, ACM Transactions on Graphics (TOG), Jul. 2010, vol. 29, Issue 4, Article 40, ACM, New York, New York, United States.

Bickel, Bernd et al., Multi-Scale Capture of Facial Geometry and Motion, ACM Transaction on Graphics (TOG), Jul. 2007, vol. 26, Issue 3, Article 33, ACM, New York, New York, United States.

Ickel, Bernd et al., Capture and Modeling of Non-Linear Heterogeneous Soft Tissue, ACM Transaction of Graphics (TOG), Aug.

(56) References Cited

OTHER PUBLICATIONS 2009, vol. 28, Issue 3, Article 89, ACM, New York, New York, United States.

Bickel, Bernd et al., Design and fabrication of materials with desires deformation behavior, ACM Transactions on Graphics (TOG), Jul. 2010, vol. 29, Issue 4, Article 63, ACM, New York, New York, United States.

Bradley, Derek. et al., Accurate multi-view reconstruction using robust binocular stereo and surface meshing, IEEE Conference on Computer Vision and Pattern Recognition, Jun. 2008, pp. 1-8, IEEE, Piscataway, New Jersey, United States.

Bradley, Derek et al., High resolution passive facial performance capture, ACM Graphics on Graphics (TOG), Jul. 2010, vol. 29, Issue 4, Article 41, ACM, New York, New York, United States.

Clarberg, Petrik et al., Wavelet Importance Sampling: Efficiently Evaluating Products of Complex Functions, ACM Graphics on Graphics (TOG), Jul. 2005, vol. 24, Issue 3, pp. 1166-1175, ACM, New York, New York, United States.

Dong, Yue et al., Fabricating Spatially-Varying Subsurface Scattering, ACM Graphics on Graphics (TOG), Jul. 2010, vol. 29, Issue 4, Article 62, ACM, New York, New York, United States.

Hasan, Milos et al., Physical Reproduction of Materials with Specified Subsurface Scattering, ACM Graphics on Graphics (TOG), Jul. 2010, vol. 29, Issue 4, Article 61, ACM, New York, New York, United States.

Irving, G. et al., Invertible Finite Elements for Robust Simulation of Large Deformation, Proceedings of the 2004 ACM SIGGRAPH/ Eurographics symposium on Computer animation, 2004, pp. 131-140, Eurographics Association, Aire-la-Ville, Geneva, Switzerland.

Kauer, M. et al., Inverse Finite Element Characterization of Soft Tissues, Medical Image Analysis, Sep. 2002, vol. 6, Issue 3, pp. 275-287, Elsevier Science B.V., Atlanta, GA, United States.

Kharevych, Lily et al., Numerical Coarsening of Inhomogeneous Elastic Materials, ACM Transactions on Graphics (TOG), Aug. 2009, vol. 28, Issue 3, Article 51, ACM, New York, New York, United States.

Kilian, Martin et al., Curved Folding, ACM Transactions on Graphics (TOG), Aug. 2008, vol. 27, Issue 3, Article 75, ACM, New York, New York, United States.

Koch, et al., Simulating Facial Surgery Using Finite Element Models, Proceedings of the 23rd annual conference on Computer graphics and interactive techniques, 1996, pp. 421-428, ACM, New York, New York, United States.

Lee, Sung-Hee et al., Heads Up! Biomechanical Modeling and Neuromuscular Control of the Neck, ACM Transactions on Graphics (TOG), Jul. 2006, pp. 1188-1198, vol. 25, Issue 3, ACM, New York, New York, United States.

Lee, Sung-Hee et al., Comprehensive Biomechanical Modeling and Simulation of the Upper Body, ACM Transactions on Graphics (TOG), Aug. 2009, vol. 28, Issue 4, Article 99, ACM, New York, New York, United States.

Levin, David, The Approximation Power of Moving Least-Squares, Mathematics of Computation, Oct. 1998, vol. 67, Issue 224, pp. 1517-1531, American Mathematical Society, Boston, MA, United States.

Li, Xian-Ying et al., Popup: Automatic Paper Architectures from 3D Models, ACM Transactions on Graphics (TOG), Jul. 2010, vol. 29, Issue 4, Article 111, ACM, New York, New York, United States.

Matsui, Daisuke et al., Generating Natural Motion in an Android by Mapping Human Motion, Proceedings of the 3rd ACM/IEEE international conference on Human robot interaction, 2008, pp. 65-72, ACM, New York, New York, United States.

Minato, Takashi et al., Development of an Android Robot for Studying Human-Robot Interaction, Proceedings of the 17th international conference on Innovations in applied artificial intelligence, 2004, pp. 424-434, Springer Verlag Inc., New York, New York, United States.

Mitani, Jun et al., Making Papercraft Toys from Meshes using Strip-based Approximate Unfolding, ACM Transactions on Graphics (TOG), Aug. 2004, pp. 259-263, vol. 23, Issue 3, ACM, New York, New York, United States.

Mori, Yuki et al., Plushie: An Interactive Design System for Plush Toys, ACM Transactions on Graphics (TOG), Jul. 2007, vol. 26, Issue 3, Article 45, ACM, New York, New York, United States.

Nesme, Matthieu et al., Preserving Topology and Elasticity for Embedded Deformable Models, Aug. 2009, vol. 28, Issue 3, Article 52, ACM, New York, New York, United States.

Oh, Jun-Ho et al., Design of Android type Humanoid Robot Albert Hubo, International Conference on Intelligent Robots and Systems, Oct. 2006, pp. 1428-1433, Piscataway, NJ, United States.

Pai, Dinesh K. et al., Scanning Physical Interaction Behavior of 3D Objects, Proceedings of the 28th annual conference on Computer graphics and interactive techniques, 2001, pp. 87-96, ACM, New York, New York, United States.

Schenk, Olaf et al., On Fast Factorization Pivoting Methods for Sparse Symmetric Indefinite Systems, ACM Transactions on Graphics (TOG), Sep. 2006, pp. 445-471, vol. 32, Issue 3, ACM, New York, New York, United States.

Sifakis, Eftychios et al., Automatic Determination of Facial Muscle Activations from Sparse Motion Capture Marker Data, ACM Transactions on Graphics (TOG), Jul. 2005, pp. 417-425, vol. 24, Issue 3, ACM, New York, New York, United States.

Sueda, Shinjiro et al., Musculotendon Simulation for Hand Animation, ACM Transactions on Graphics (TOG), Aug. 2008, vol. 27, Issue 3, Article 83, ACM, New York, New York, United States.

Teran, J. et al., Creating and Simulating Skeletal Muscle from the Visible Human Data Set, IEEE Transactions on Visualization and Computer Graphics, May 2005, pp. 317-328, vol. 11, Issue 3, IEEE Educational Activities Department, Piscataway, NJ, United States.

Terzopoulos, Demetri et al., Analysis and Synthesis of Facial Image Sequences Using Physical and Anatomical Models, IEEE Transactions on Pattern Analysis and Machine Intelligence, Jun. 1993, pp. 569-579, vol. 15, Issue 6, IEEE Computer Society, Washington, DC, United States.

Terzopoulos, Demetri et al., Elastically Deformable Models, ACM SIGGRAPH Computer Graphics, Jul. 1987, pp. 205-214, vol. 21, Issue 4, ACM, New York, New York, United States.

Thoutireddy, P. et al., A Variational r-Adaption and Shape-Optimization Method for Finite-Deformation Elasticity, International Journal for Numerical Methods in Engineering, Sep. 2004, pp. 1-21, vol. 61, Issue 1, John Wiley & Sons, Ltd., Malden, MA, United States.

Van Gelder, Allen, Approximate Simulation of Elastic Membranes by Triangulated Spring Meshes, Journal of Graphics Tools, Feb. 1998, pp. 21-42, vol. 3, Issue 2, A.K. Peters, Ltd., Natick, MA, United States.

Wang, Yang et al., High Resolution Acquisition, Learning and Transfer of Dynamic 3-D Facial Expressions, Computer Graphics Forum, 2004, pp. III: 677-686, EuroGraphics, Geneva, Switzerland.

Weyrich, Tim et al., Fabricating Microgeometry for Custom Surface Reflectance, ACM Transactions on Graphics (TOG), Aug. 2009, vol. 28, Issue 3, Article 32, ACM, New York, New York, United States.

Valdivia, Pablo et al., Performance of Machines with Flexible Bodies Designed for Biomimetic Locomotion in Liquid Environments, International Conference on Robotics and Automation, Apr. 2005, pp. 3324-3329, Barcelona, Spain.

Zhang, Li et al., Spacetime Faces: High Resolution Capture for Modeling and Animation, ACM Transactions on Graphics (TOG), Aug. 2004, pp. 548-558, vol. 23, Issue 3, ACM, New York, New York, United States.

Zordan, Victor B. et al., Breathe Easy: Model and control of simulated respiration for animation, Proceedings of the 2004 ACM SIGGRAPH/Eurographics symposium on Computer animation, 2004, pp. 29-37, Eurographics Association, Aire-la-Ville, Geneva, Switzerland.

Gourret, Jean-Paul et al., Simulation of Object and Human Skin Deformations in a Grasping Task, International Conference on Computer Graphics and Interactive Techniques, 1989, pp. 21-30, ACM, New York, New York, United States.

(56) References Cited

OTHER PUBLICATIONS

Hara, Fumio et al., Realistic Facial Expressions by SMA Driven Face Robot, International Workshop on Robot and Human Interactive Communication, Sep. 2001, pp. 504-511, IEEE, Piscataway, NJ, United States.

Terada, Yuuzi et al., An Animatronic System Including Lifelike Robotic Fish, Proceedings of the IEEE, Nov. 2004, pp. 1814-1820, vol. 92, No. 11, IEEE, Piscataway, NJ, United States.

Nocedal, Jorge et al., Newton's Method With Hessian Modification, Numerical Optimization (Springer Series in Operations Research and Financial Engineering), 2006, pp. 48-52, Springer Science+Business Media, LLC, New York, New York, United States.

* cited by examiner

PHYSICAL FACE CLONING

CROSS-REFERENCE TO RELATED APPLICATIONS

This application is a continuation of U.S. patent application Ser. No. 13/275,481 filed Oct. 18, 2011, now Pat. No. 9,082,222, which claims the benefit of U.S. Provisional Patent Application No. 61/433,923, filed on Jan. 18, 2011, each of which are incorporated herein by reference in its entirety.

BACKGROUND

Field of the Invention

The present invention relates to the field of animatronics and, in particular, to a system and method for computer graphics modeling to clone physical faces.

Description of the Related Art

Generally, the field of animatronics aims to create physical robotic characters that move and look like real humans. Because the human body consists of articulated rigid structures (i.e., bones) and soft tissue (i.e., flesh and skin), conventional approaches have used a rigid articulated base and synthetic soft-tissue to create animatronic characters. Characters created with this approach have enjoyed wide success at amusement parks, theme parks, and exhibitions.

However, creating animatronic figures remains a difficult and labor-intensive process that requires a significant amount of manual work of skilled animators, material designers, and mechanical engineers. The physical constraints of real materials and actuators, in addition to virtual modeling of a human character, must be addressed to create a life-like animatronic character. Further, the human face is regarded as the most challenging part of creating an animatronic character, owing to the face's expressive power and to the limitations in the process of skin design. An animatronic character has to be able to produce a vast range of facial expressions, each having different folds and wrinkles. Manually designing the shape and material properties of a single skin that is able to achieve suitable expression is a formidable task.

As the foregoing illustrates, there is a need in the art for an improved technique for designing and fabricating an animatronic face that closely resembles a given human subject.

SUMMARY

Embodiments of the invention provide a technique for physical face cloning that uses facial performance capture, physics-based simulation, and fabrication-oriented material design to model, optimize, and fabricate synthetic skin for animatronic characters. Embodiments of the invention provide a processing pipeline that accepts a number of captured input data. For example, elastic material properties are captured for a range of possible synthetic skin materials using a custom measurement system. In another example, a collection of different facial expressions is captured for a given target human face. The captured input data is then fed into a computational model that simulates deformation behavior of a synthetic skin. An optimization process is provided herein to generate and optimize a synthetic skin geometry and actuation parameters of the underlying animatronics device using the computational model to provide a closer match to the target human face. The described processing pipeline may be validated by fabricating a synthetic silicone skin according to the optimized skin geometry and animating the skin on an articulated robot head using the optimized actuation parameters.

One embodiment of the invention provides a computer-implemented method for generating an object shape. The method includes determining one or more target surfaces, generating a surface geometry comprising an outer surface and an inner surface, and modifying the inner surface based on a computational model such that the outer surface of the surface geometry more closely matches the target surface when the surface geometry is deformed.

Another embodiment of the invention provides a computer-implemented method for defining a physical skin for a deformable object. The method includes capturing a plurality of expressive poses for a target object and generating a computational model based on a plurality of material parameters for a material. In one embodiment, the computational model simulates deformation behavior of a fabricated object comprised of the material. The method further includes modifying a shape geometry based on the computational model and the plurality of expressive poses. The shape geometry may be modified such that the shape geometry more closely matches each of the plurality of expressive poses when deformed.

One advantage of embodiments of the invention is the ability to generate an animatronics face that closely results a given human subject using an automated process that reduces costly trial and error incurred by iterations of physical models. Additionally, embodiments of the invention provide increased realism of the resulting animatronic face.

BRIEF DESCRIPTION OF THE DRAWINGS

So that the manner in which the above recited features of the invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the invention provide a technique for physical face cloning that uses facial performance capture, physics-based simulation, and fabrication-oriented material design to model, optimize, and fabricate synthetic skin for animatronics characters. Embodiments of the invention provide a processing pipeline that accepts a number of captured input data. For example, facial expression poses are captured for a given target human face. In another example, elastic material properties are captured for a range of possible synthetic skin materials using a custom measurement system. The captured input data is incorporated into a computational model that simulates deformation behavior of a synthetic skin.

Embodiments of the invention provide techniques for modifying, sometimes referred to as "optimizing", a skin geometry, actuation parameters, and other parameters to provide a closer match to a target shape as compared to prior to the modification. One embodiment of the invention provides a computer-implemented method to generate and optimize a synthetic skin geometry and actuation parameters of an underlying animatronics device that provide a best or closer match to a collection of given target expressions. Another embodiment of the invention provides a process for physical reproduction of a human face on an animatronics device, including data acquisition, physical simulation, optimization, fabrication, and validation.

Figure 1:
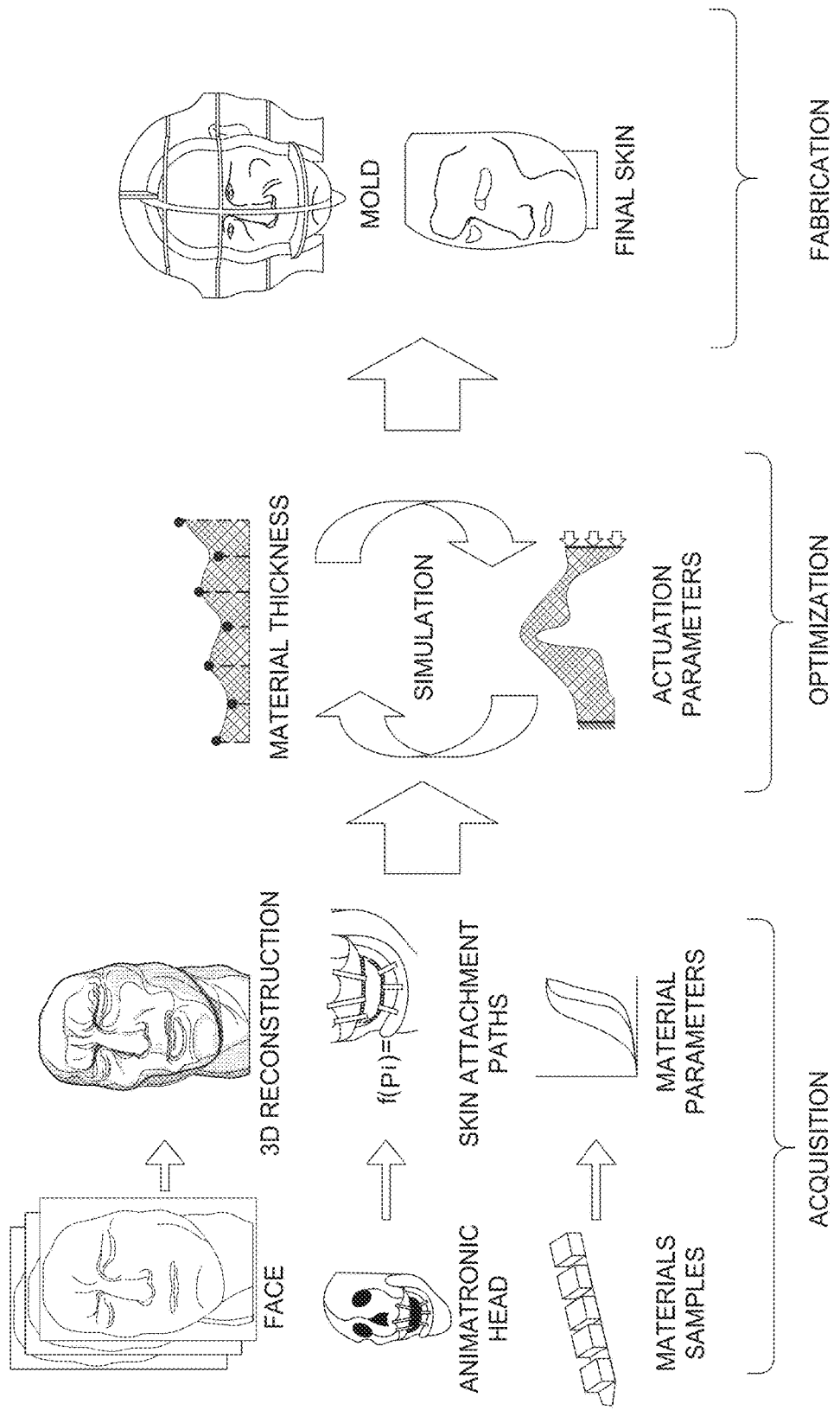
FIG. 1 is a conceptual diagram illustrating a processing pipeline, according to one embodiment of the invention.

FIG. 1 is a conceptual diagram illustrating a processing pipeline, according to one embodiment of the invention. As shown, the processing pipeline generally includes an acquisition phase, an optimization phase, and a fabrication phase.

During the acquisition phase, a variety of input data is captured and/or obtained for use in a computational simulation described in detail herein. In one embodiment, facial expressions of a human subject may be captured as 3D reconstructions using an optical performance capture system. The 3D reconstructions may comprise high-resolution data that includes data about pores and wrinkles of the subject's skin, as well as robust temporal correspondence, to provide information about the deformation behavior of the human subject's skin. In one embodiment, as shown, an operational range of an animatronic head comprised of skin attachment links actuated by motors may be captured as one or more functions representing skin attachment paths. Accordingly, the captured target shapes of the human face and the captured description of the animatronic head, as acquired during the acquisition phase, may be utilized to design synthetic soft tissue that matches the captured target shapes as closely as possible.

One base material contemplated for the synthetic skin is silicone, which offers a wide range of stiffness that can be controlled by adjusting a number of material parameters, such as the concentration of plasticizer in the compound. In one embodiment, elastic material properties are captured for a range of possible synthetic skin materials using a custom measurement system. As shown, the elastic material properties may be utilized to determine one or more material parameters for a synthetic skin simulation model by numerically fitting the computational model to the experimentally acquired force-displacement samples of materials with different stiffness.

During the optimization phase, a synthetic skin geometry and actuation parameters may be generated to match the target facial expressions captured during the acquisition phase. The outer surface of the synthetic skin, in the undeformed configuration, may be determined using a captured 3D scan of the target face in a neutral target pose. According to embodiments of the invention, the inner surface (i.e., thickness) of the synthetic skin may be varied to achieve spatially varying stiffness and deformation behavior.

Embodiments of the invention provide a computational model that simulates the deformation behavior of a synthetic skin having a particular geometry using the input data acquired during the acquisition phase. In one embodiment, a nonlinear finite element method in combination with a neo-Hookean material, described later, may be used to model and simulate the deformation behavior of the synthetic skin. The forward simulation allows accurate prediction of the deformed shape of a given synthetic skin and the resulting forces induced by the moving skin attachment links. Accordingly, a skin geometry having a variable material thickness may be generated using the simulation model to best match a desired target expression. Furthermore, actuation parameters of the animatronic device may be optimized to find parameters that best resemble each individual target expression. According to one embodiment of the invention, the various degrees of freedom described herein may be handled in a single uniform optimization framework, described in detail below.

During the fabrication phase, the skin geometry and actuation parameters generated during optimization phase may be validated by fabricating various silicone objects using, for example, injection molding. In one embodiment, the molds used for injection molding may be created using a rapid prototyping 3D printer. Real-world behavior of the fabricated skin may be tested and compared to the predicted simulation results for different deformation scenarios.

System Overview

Figure 2:
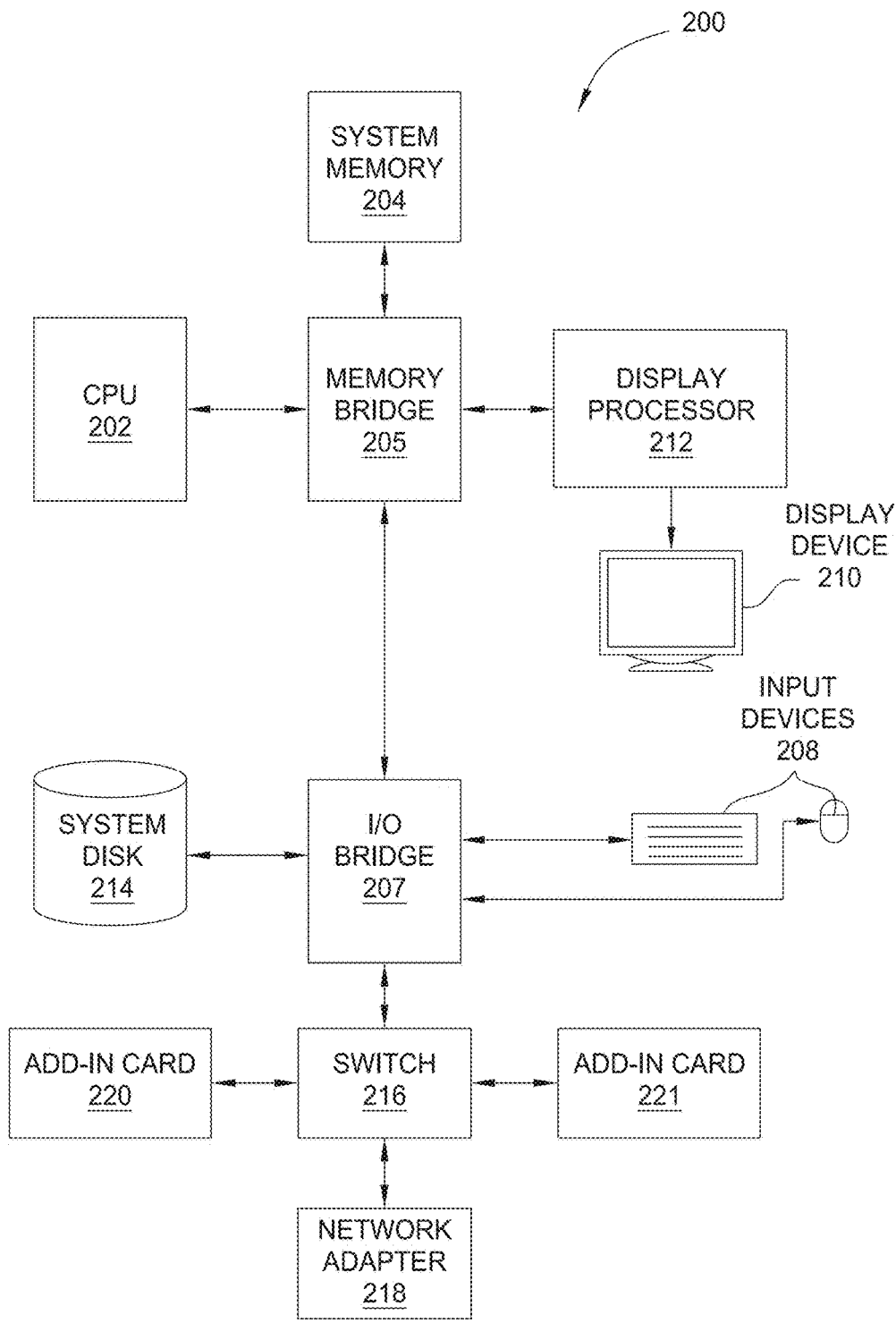
FIG. 2 is a block diagram of a system configured to implement one or more aspects of the present invention.

FIG. 2 is a block diagram of a system 200 configured to implement one or more aspects of the present invention. System 200 may be a computer workstation, personal computer, video game console, personal digital assistant, rendering engine, mobile phone, or any other device suitable for practicing one or more embodiments of the present invention.

As shown, system 200 includes a central processing unit (CPU) 202 and a system memory 204 communicating via a bus path that may include a memory bridge 205. CPU 202 includes one or more processing cores, and, in operation, CPU 202 is the master processor of system 200, controlling and coordinating operations of other system components. System memory 204 stores software applications and data for use by CPU 202. CPU 202 runs software applications and optionally an operating system. Memory bridge 205, which may be, e.g., a Northbridge chip, is connected via a bus or other communication path (e.g., a HyperTransport link) to an I/O (input/output) bridge 207. I/O bridge 207, which may be, e.g., a Southbridge chip, receives user input from one or more user input devices 208 (e.g., keyboard, mouse, joystick, digitizer tablets, touch pads, touch screens, still or video cameras, motion sensors, and/or microphones) and forwards the input to CPU 202 via memory bridge 205.

A display processor 212 is coupled to memory bridge 205 via a bus or other communication path (e.g., a PCI Express, Accelerated Graphics Port, or HyperTransport link); in one embodiment display processor 212 is a graphics subsystem that includes at least one graphics processing unit (GPU) and graphics memory. Graphics memory includes a display memory (e.g., a frame buffer) used for storing pixel data for each pixel of an output image. Graphics memory can be integrated in the same device as the GPU, connected as a separate device with the GPU, and/or implemented within system memory 204.

Display processor 212 periodically delivers pixels to a display device 210 (e.g., a screen or conventional CRT, plasma, OLED, SED or LCD based monitor or television). Additionally, display processor 212 may output pixels to film recorders adapted to reproduce computer generated images on photographic film. Display processor 212 can provide display device 210 with an analog or digital signal.

A system disk 214 is also connected to I/O bridge 207 and may be configured to store content and applications and data for use by CPU 202 and display processor 212. System disk 214 provides non-volatile storage for applications and data and may include fixed or removable hard disk drives, flash memory devices, and CD-ROM, DVD-ROM, Blu-ray, HD-DVD, or other magnetic, optical, or solid state storage devices. According to one embodiment of the invention, the system disk 214 may store graphical data, such as captured 3D reconstructions, and acquired data such as material parameters, skin attachment paths, and pre-computations according to certain aspects of the invention.

A switch 216 provides connections between I/O bridge 207 and other components such as a network adapter 218 and various add-in cards 220 and 221. Network adapter 218 allows system 200 to communicate with other systems via an electronic communications network, and may include wired or wireless communication over local area networks and wide area networks such as the Internet.

Other components (not shown), including USB or other port connections, film recording devices, and the like, may also be connected to I/O bridge 207. For example, an audio processor may be used to generate analog or digital audio output from instructions and/or data provided by CPU 202, system memory 204, or system disk 214. Communication paths interconnecting the various components in FIG. 2 may be implemented using any suitable protocols, such as PCI (Peripheral Component Interconnect), PCI Express (PCI-E), AGP (Accelerated Graphics Port), HyperTransport, or any other bus or point-to-point communication protocol(s), and connections between different devices may use different protocols, as is known in the art.

In one embodiment, display processor 212 incorporates circuitry optimized for graphics and video processing, including, for example, video output circuitry, and constitutes a graphics processing unit (GPU). In another embodiment, display processor 212 incorporates circuitry optimized for general purpose processing. In yet another embodiment, display processor 212 may be integrated with one or more other system elements, such as the memory bridge 205, CPU 202, and I/O bridge 207 to form a system on chip (SoC). In still further embodiments, display processor 212 is omitted and software executed by CPU 202 performs the functions of display processor 212.

Graphical data for physical face cloning can be provided to display processor 212 directly from CPU 202. In some embodiments of the present invention, the display processor 212 may perform graphical processing on one or more 3D reconstructions to display and/or de-construct the 3D reconstruction into a representative data structure.

In one embodiment, CPU 202 provides display processor 212 with data and/or instructions defining the captured performance of a target human subject, from which display processor 212 processes as 3D reconstructions of expressive poses for processing according to embodiments of the invention. The data and/or instructions defining the 3D reconstructions can be stored in system memory 204 or graphics memory within display processor 212. In an embodiment, display processor 212 includes 3D rendering capabilities for generating pixel data for output images from instructions and data defining the geometry, lighting shading, texturing, motion, and/or camera parameters for a scene.

Display processor 212 can further include one or more programmable execution units capable of executing shader programs, tone mapping programs, and the like. In one embodiment, the CPU 202 may be configured to determine a simulation model configured to simulate deformation behavior of one or more subject objects having a given geometry based on a plurality of material parameters. In another embodiment, the CPU 202 may further be configured to optimize a skin geometry of synthetic skin such that the synthetic skin matches one or more of the expressive poses when deformed.

It will be appreciated that the system shown herein is illustrative and that variations and modifications are possible. The connection topology, including the number and arrangement of bridges, may be modified as desired. For instance, in some embodiments, system memory 204 is connected to CPU 202 directly rather than through a bridge, and other devices communicate with system memory 204 via memory bridge 205 and CPU 202. In other alternative topologies display processor 212 is connected to I/O bridge 207 or directly to CPU 202, rather than to memory bridge 205. In still other embodiments, I/O bridge 207 and memory bridge 205 might be integrated into a single chip. The particular components shown herein are optional; for instance, any number of add-in cards or peripheral devices might be supported. In some embodiments, switch 216 is eliminated, and network adapter 218 and add-in cards 220, 221 connect directly to I/O bridge 207.

According to embodiments of the invention, a synthetic skin geometry and actuation parameters may be optimized to best match a target set of facial expressions. Certain embodiments of the invention may be implemented in software stored in system memory 204 and executed by CPU 202 and/or display processor 212. Other embodiments may be implemented as one or more shader programs executed by display processor 212. Still further embodiments may be implemented in fixed function hardware included within display processor 212. Other embodiments may be implemented as a combination of hardware and software.

Physical Face Cloning

Figure 3:
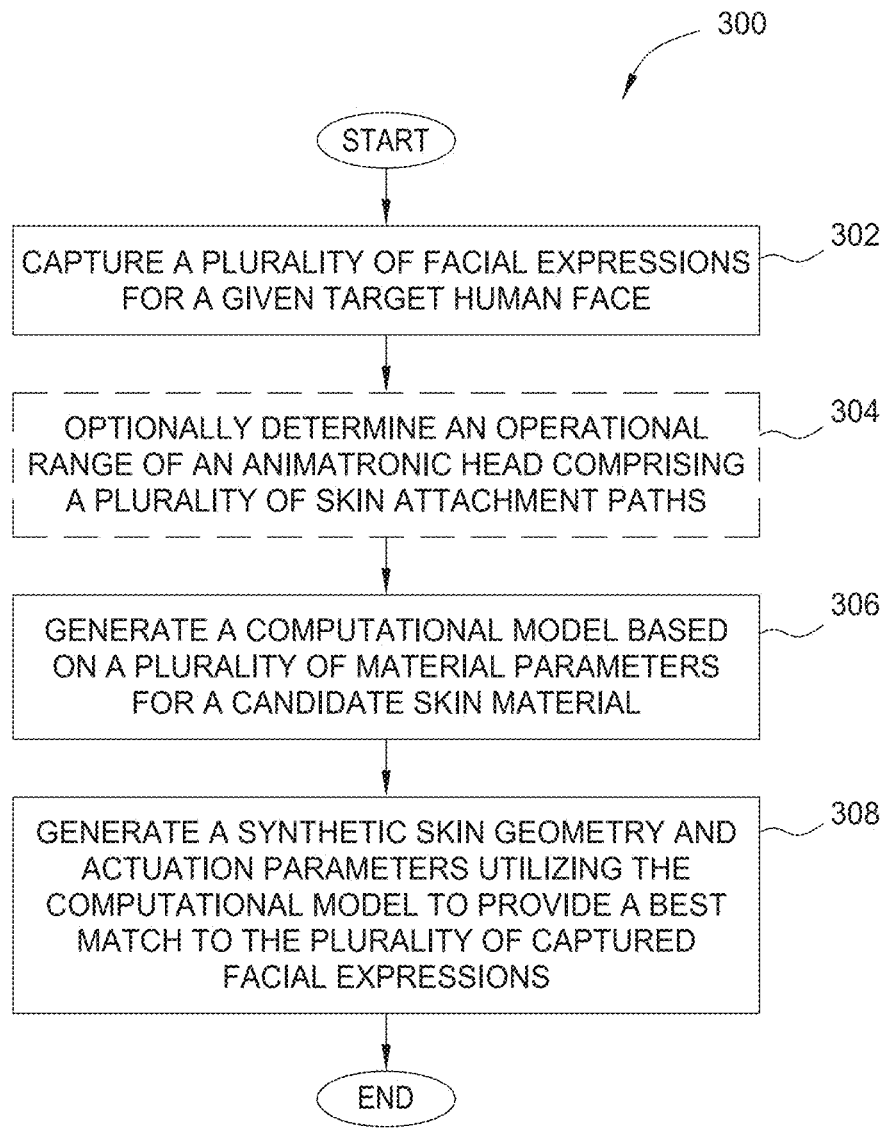
FIG. 3 is a flow diagram of method steps for physical face cloning, according to one embodiment of the invention.

FIG. 3 is a flow diagram of method steps for defining a physical skin for a deformable object, according to one embodiment of the invention. Persons skilled in the art will understand that, even though the method 300 is described in conjunction with the systems of FIGS. 1-2, any system configured to perform the method steps, in any order, is within the scope of embodiments of the invention.

As shown, the method 300 begins at step 302, where a processor captures a plurality of facial expressions for a given target human face. Matching the shape of the face and how the skin deforms under different facial expressions is one of the chief challenges to cloning a human face. As such, various 3D expressions of a subject to be cloned may be reconstructed to seed the deformable skin optimization technique described herein. While embodiments of the invention discuss examples of replicating human faces, it is understood that embodiments of the invention also include frameworks and techniques for replicating realistic fully-body characters.

A short performance of the target subject may be captured using a high resolution method for face scanning. In one embodiment, a high resolution marker-less geometry acquisition method may be utilized with an optical flow based approach to temporal alignment to generate a detailed, compatible mesh sequence with explicit temporal correspondence. It other embodiments, other suitable technically feasible techniques for capturing facial expressions may be implemented, such as a marker-based motion capture system, or a structure-light system. The generated mesh sequence allows for analysis of the deformation of a face under various expressions, down to the level of individual skin wrinkles. In one embodiment, a number of expressive poses from the mesh sequence are chosen for optimizing the skin parameters. A subset of the captured facial expressions is shown in FIG. 4.

Figure 4:
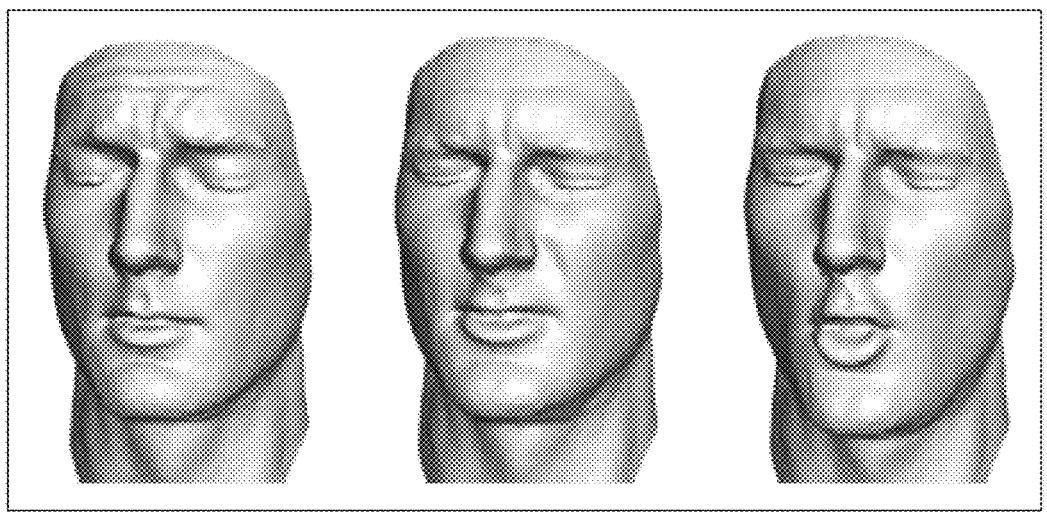
FIG. 4 is a conceptual illustration of 3D (three-dimensional) facial expressions captured according to one embodiment of the invention.

FIG. 4 is a conceptual illustration of 3D facial expressions captured according to one embodiment of the invention. In one embodiment, a captured facial expression comprises a detailed representation of a human head, including major features such as nose, ears, eyes, mouth, eye brow, as well as fine details, such as skin wrinkles, hairs, pores, and imperfections. The captured facial expression may represent a neutral pose or may represent an expressive pose wherein one or more of the facial features of the face are distorted, articulated, actuated, and/or deformed. In one embodiment, the 3D facial expressions may comprise 3D reconstructions represented and stored as geometrical mesh structures suitable for processing and manipulation according to embodiments of the invention.

Returning to FIG. 3, the method 300 continues at step 304, where a processor may optionally determine an operational range of an animatronic head, the operational range comprising a plurality of skin attachment paths. In one embodiment, an operational range of an animatronic head comprised of a set of skin attachment links actuated by motors may be captured as one or more functions representing skin attachment paths. In one implementation, a marker may be attached to each moving link of the animatronic head, and a mapping of actuation parameters (i.e., $p_{act}$) to a 3D location and orientation of each link in space is sampled. Interpolating these samples may yield a continuous function (i.e., $m(p_{act})$) that describes the path of the skin attachment links. In some embodiments, step 304 is optional and is omitted, as indicated by the dotted box around step 304 in FIG. 3.

At step 306, the processor generates a computational model based on a plurality of material parameters for a candidate skin material. As part of the face cloning pipeline described herein, an accurate computational model may be determined for simulating deformations of a synthetic skin. According to one embodiment, a computational model may be generated that models skin as a hyperelastic isotropic solid. In one embodiment, finite-deformation continuum mechanics may be utilized to account for large rotations, stretching, and compression that may be exhibited by synthetic skin for use with animatronic devices.

In one embodiment, a computational model may be derived as follows. Let X and x denote smooth functions describing the position of a synthetic skin in an undeformed and deformed state, respectively. Further, let $\varphi:\Omega \rightarrow \mathfrak{R}^3$ denote a mapping that transforms material points from the undeformed configuration to the deformed configuration as $x=\varphi(X)$. The deformation of the skin at each point may be characterized by a deformation gradient F, or alternatively, a right Cauchy-Green tensor C, which are defined as:

$$F = \frac{\partial \varphi}{\partial X}, \text{ respectively } C = F^T F.$$

According to one embodiment, for a hyperelastic material, the energy of a solid depends only on its current state of deformation, which may be described in a rotation-invariant and frame-invariant manner through the tensor C. A corresponding energy density function may be denoted by $\Psi=\Psi(C)$. The relation between $\Psi$ and C is described by a material model, described further below.

Generally, animating expressions on a virtual face induces both finite stretching and compression of the synthetic skin. The synthetic skin may be comprised of a rubber-like substance such as silicone, which may be adequately modeled as elastic materials with isotropic and homogenous properties. In one embodiment, a hyperelastic material model, such as a neo-Hookean material model, may be generated to predict the stress-strain behavior of a synthetic skin comprised of silicone. For example, in a simple representative of this class of material models, the strain energy density of a compressible neo-Hookean material may be given as:

$$\Psi(C) = \frac{\mu}{2}\left(J^{-\frac{2}{3}}tr(C) - 3\right) - \frac{\kappa}{2}(J - 1)^2, \quad (1)$$

where J=det F, and $\mu$, $\kappa$ are shear and bulk moduli, which are related to Young's modulus E and Poisson's ratio $\nu$ as:

$$E = \frac{9\mu\kappa}{3\kappa + \mu}, \text{ respectively } \nu = \frac{3\kappa - 2\mu}{2(3\kappa + \mu)}. \quad (2)$$

While the neo-Hookean material model only provides for two parameters, it has been determined that such a model, given the range of deformations considered in embodiments of the invention, is sufficiently accurate for obtaining strong correspondence with the measured data. In other embodiments, any suitable material models may be utilized to describe the relation between $\Psi$ and C, described above.

According to one aspect, given a determined material model, the material parameters $\mu$ and $\kappa$ for a given material sample may be determined using a variety of techniques described herein. In one embodiment, a vision-based acquisition system may be utilized to capture dense surface displacement fields of material samples and determine optimal material parameters by minimizing the displacement error of a corresponding finite element approximation. In other embodiments, other techniques for fitting measured data to computational models may be utilized, such as techniques for linear-elastic materials, nonlinear viscoelastic soft tissue, nonlinear heterogeneous materials, etc.

In one embodiment, silicone rubber may be selected as a base material for fabricating synthetic skin because it is easily processed and offers a vast range of stretch resistance. In other embodiments, other candidate materials having suitable elasticity may be utilized for fabricating synthetic skin according to certain aspects of the present disclosure. An animatronics device as described herein may exert a limited force through its actuators, which imposes an upper bound on the net stiffness of the synthetic skin. Therefore, the silicone composition may be adjusted such that the net stiffness of the synthetic skin complies with these constraints. To accomplish this task, a technique is provided for determining the material parameters necessary to produce a suitable silicone composition. In one embodiment, a series of experiments may first be conducted to measure the force-deformation behavior of a collection of silicone samples with different amounts of plasticizer. Then, numerical optimization may be performed in order to determine the material parameters of a computational model that best matches the experimental data.

According to one embodiment, the measurement of force-deformation behavior may be empirically conducted by pulling on small samples of a given candidate material having a given set of elastic material properties with a controlled force and capturing the resulting deformation over time. In one embodiment, stereo reconstruction may be utilized to determine a corresponding reconstruction based on a capture image of a deformed square sample. With a set of applied forces (i.e., loads) and the corresponding surface displacements determined, the material parameters may be optimized for a finite element solver in order to best approximate the measured stress-strain behavior. In one embodiment, an objective function $O(p)=\Sigma_i|(\tilde{x}_i - x_i(p))^2|$ that measures the difference between simulated surface positions $x_i$ (p) and their closest corresponding point of the capture surface $\tilde{x}_i$. The vector p comprises physical parameters of the material model, which may be identified using Young's modulus and Poisson's ratio, described above. Given an initial guess $p_0$, a processor iteratively computes updated parameters in a simulated annealing process. In each iteration, the processor computes the finite element solution $x_i(p)$ with the current parameters, evaluates the objective function O(p), and determines the updated parameters $p_{i+1}$. This process may be reiterated until the objective function O(p) signals convergence.

According to one embodiment, the numerical-experimental material fitting process described above may be validated by comparing stress-strain curves obtained from a standard testing procedure, such as ISO 37, to those obtained from a virtual counterpart of the same experiment. In one example, it has been determined that real-world material behavior matches closely for strain (i.e., deformations) in the range of −20% to 50%. Considering the operating range of an animatronic device according to embodiments of the invention, this behavior permits a sufficiently large safety margin for error.

In one embodiment, an optimization process described further in FIG. 6 below may use minimization of the elastic energy subject to boundary conditions. As such, Equation (1) may be discretized in space using tetrahedral finite elements. For example, let $x_a \in \mathfrak{R}^3$, $1 \le a \le n$ denote deformed positions of a tetrahedral mesh. For clarity, the superscript e will be used in the foregoing discussion to identify quantities pertaining to a given tetrahedral element. In particular, let $X^e \in \mathfrak{R}^{12}$ and $x^e \in \mathfrak{R}^{12}$ denote position vectors for a given element in its un-deformed and deformed state, respectively. In one embodiment, a configuration mapping may be approximated as $\varphi \approx \Sigma_a x_a N_a$ where $N_a$ are piece-wise linear basis functions associated with the nodes of the mesh. The discrete deformation gradient for each element e is then expressed as $$F^e = F(x^e, X^e) = \sum_{a=1}^{4} x_a^e \left(\frac{\partial N_a^e}{\partial X}\right)^T, \quad (3)$$

where it may be emphasized that for each element $F^e$ is a function of its position in both un-deformed and deformed configuration. All other discrete qualities required for computing the elastic energy of a deformed element seen in Equation 1, i.e. tr($C^e$) and $J^e$, follow directly from Equation (3). Furthermore, it is noted that the deformation gradient is constant within each element since $N_a^e$ are piece-wise linear functions.

Accordingly, with this relation established, the discrete energy of a deformed element We may be expressed as $$W^e(x^e, X^e) = \int_{\Omega^e} \Psi(F^e) = \Psi(F^e) V^e(X^e), \quad (4)$$

where $\Omega^e$ is the element's parameter domain and $V^e$ is its un-deformed volume. For clarity, from now on, let $x=(x_1^T, \ldots, x_n^T)^T$ and $X=(X_1^T, \ldots, X_n^T)^T$ denote vectors containing all deformed and undeformed positions, respectively. Summing up all elemental contributions, the total energy for a deformed configuration may be obtained via Equation (5) as follows:

$$W(x, X) = \sum_e W^e(x^e, X^e) \quad (5)$$

In one embodiment, this energy may be utilized in a static equilibrium problem in order to compute the deformation of the skin in response to actuator placements, which may translate into a set of position constraints. The deformed configuration of the skin is then determined as the minimum of the total energy via Equation (6) as follows:

$$x = \underset{x}{\mathrm{argmin}}\Big(W(x, X) + W_{ext}(x)\Big), \quad (6)$$

where $W_{ext}$ summarizes external contributions to the potential, e.g., due to gravity. In one embodiment, requiring the gradient of the energy to vanish at equilibrium leads to a set of nonlinear equations, which may be solved utilizing known computational approaches, such as using Newton iterations with incremental loading and line search for convergence control. Accordingly, by solving for Equation (6), skin deformation may be simulated in response to arbitrary actuator placements.

Figure 5:
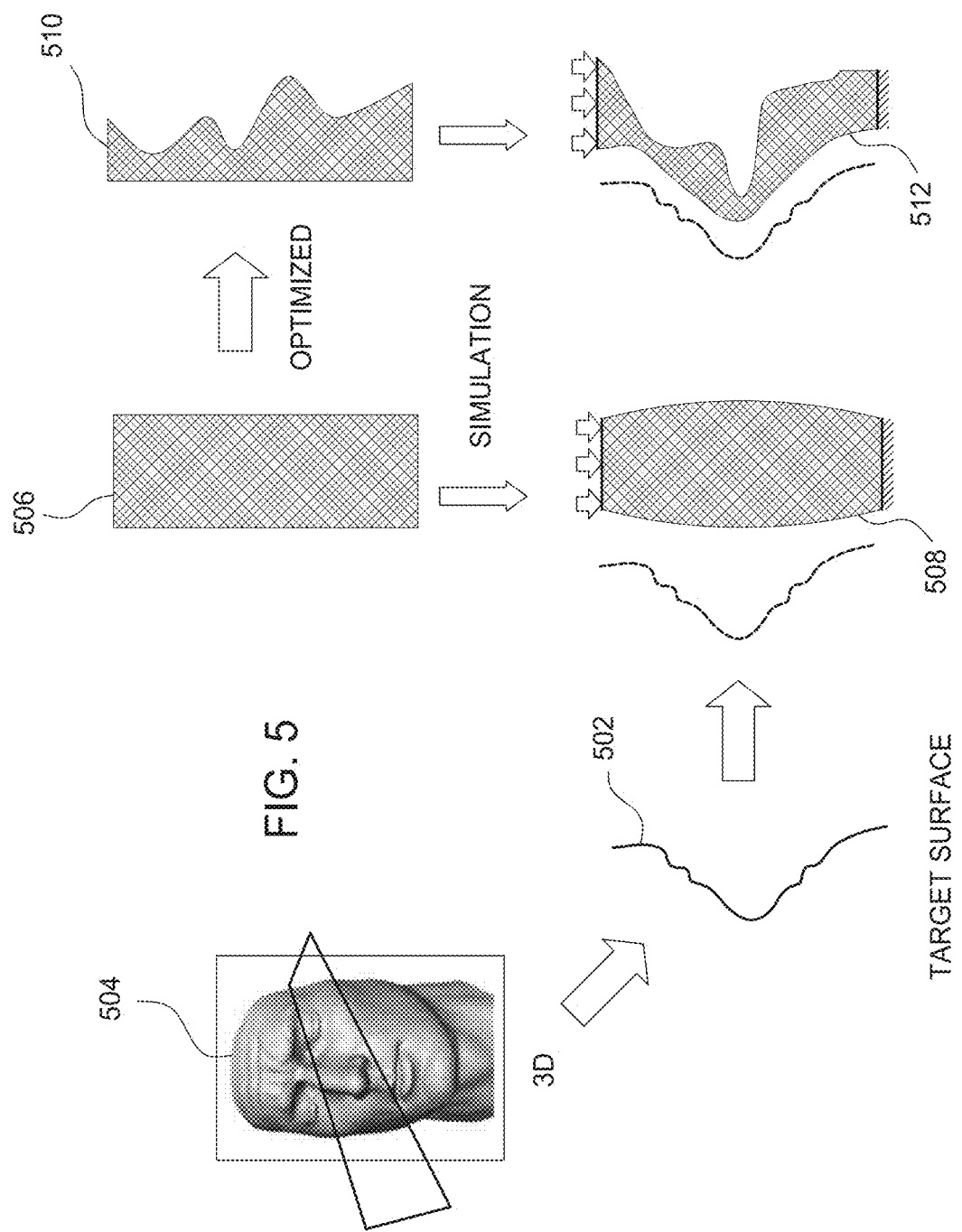
FIG. 5 is a conceptual diagram illustrating an optimization method for synthetic skin geometry according to one embodiment of the invention.

The method 300 continues at step 308, where the processor generates a synthetic skin geometry and actuation parameters utilizing the computational model to provide a better or best match to the plurality of captured facial expressions. FIG. 5 is a conceptual diagram illustrating an optimization method for synthetic skin geometry according to one embodiment of the invention. In one embodiment, one or more target surfaces 502 may be extracted and/or determined from the 3D reconstructions 504 of a human subject. An un-optimized skin patch 506 (i.e., a portion of the synthetic skin geometry) having a uniform thickness may be processed by a computational model that simulates deformation behavior of the skin patch under load. As illustrated, the deformed shape 508 of the un-optimized skin patch as deformed by a vertical load may not closely match the target surface 502, seen in outline. Accordingly, the skin patch 506 may be processed according to the optimization process described herein to generate an optimized skin patch 510 having a varying inner surface (i.e., material thickness). A deformation of the optimized skin patch 510 may be simulated according to the computational model and the resultant deformed shape 512 may be compared to the target surface 502. As shown, the optimization process determines an optimized skin geometry such that the skin has a shape and geometry that closely matches target surfaces when deformed. In one embodiment, the synthetic skin geometry and actuation parameters are optimized utilizing an optimization process shown and described in detail in FIG. 6.

Optimization Process

According to one embodiment, a skin shape (i.e., geometry), as well as the actuation parameters may be determined such that a synthetic skin fabricated to the skin shape and deformed by an underlying electromechanical base according to the actuation parameters, matches the target facial expressions as closely as possible. This process may be subject to a number of constraints. For example, the outside surface of the skin is generally configured to closely match the target human face. In another example, attachment points for the underlying facial motor actuators may not be modifiable. In yet another example, the motion of the facial motor actuators may be physically restricted. As such, in one embodiment, to better achieve results given these constraints, the animatronic face may be optimized with respect to one or more set of parameters. A generic optimization framework according to embodiments of the invention is described herein, followed by application of the described framework to specific parameters. In one embodiment, actuation parameters of the animatronic device may be optimized for each target expression. In one embodiment, thickness of the synthetic skin may be optimized by modifying the shape of the skin on the inside.

Figure 6:
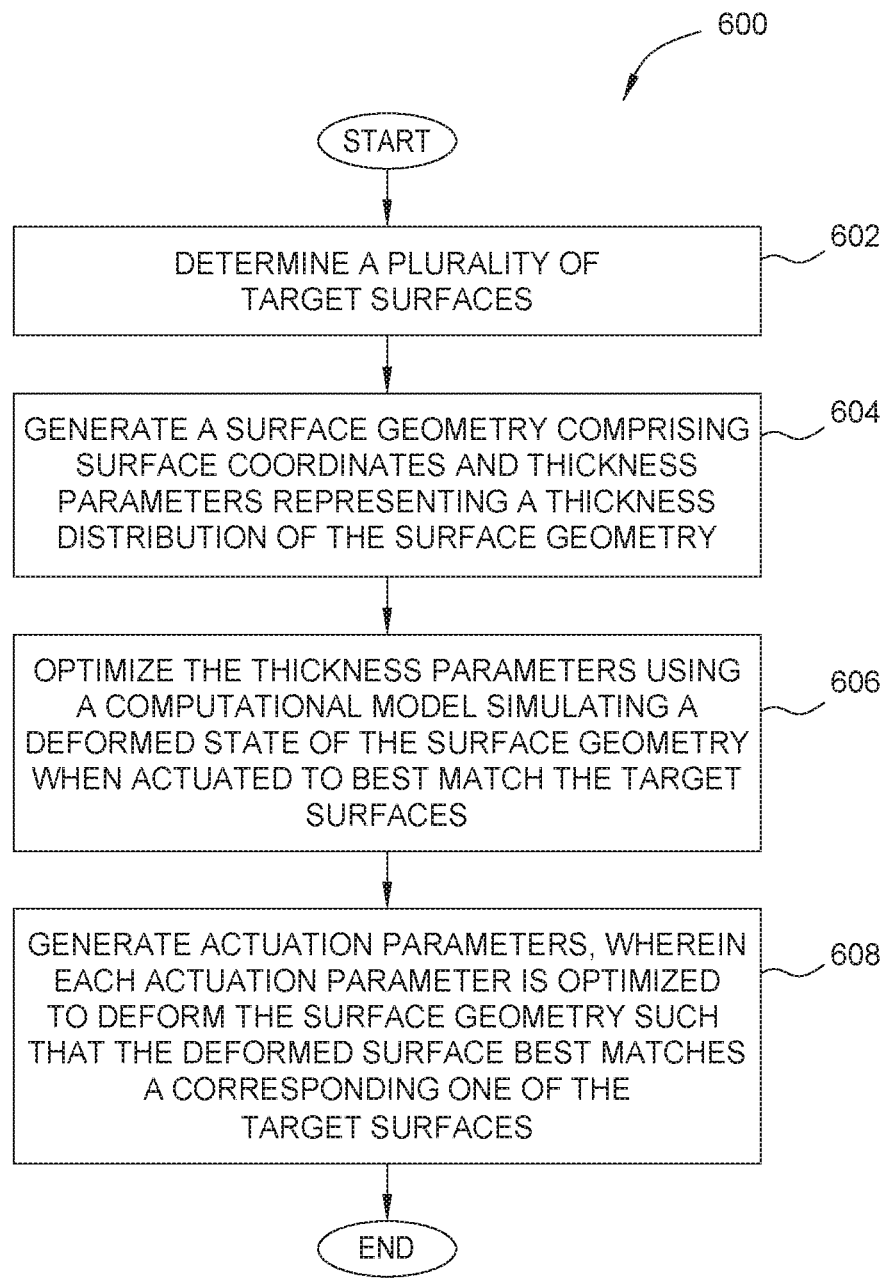
FIG. 6 is a flow diagram of method steps for optimizing skin geometry according to one embodiment of the invention.

FIG. 6 is a flow diagram of method 600 for optimizing skin geometry according to one embodiment of the invention. Persons skilled in the art will understand that, even though the method 600 is described in conjunction with the system of FIG. 2, any system configured to perform the method steps, in any order, is within the scope of embodiments of the invention.

The method 600 begins at step 602, where a processor may determine a plurality of target surfaces. In one embodiment, the plurality of target surfaces may be acquired using facial scanning to generate one or more 3D images of a human subject, as described above. In one embodiment, the plurality of target surfaces may be reconstructed three-dimensionally (i.e., 3D reconstructions) from multiple simultaneous image captures of the human subject.

According to embodiments of the invention, each target surface represents a separate target expressive pose of the human subject. The target surfaces may be represented by various data structures suitable for processing, refinement, and optimization. In one embodiment, the plurality of target surfaces may be a mesh sequence having temporal correspondence. In another embodiment, the target surface may comprise a plurality of tetrahedral structures. In one embodiment, each target surface comprises a tetrahedral mesh having a plurality of vertices, each vertex comprising a 3D point and a surface normal.

The method 600 continues at step 604, wherein the processor generates a surface geometry comprising surface coordinates and one or more thickness parameters representing a thickness distribution of the surface geometry. According to one embodiment, the surface geometry may comprise an outer surface and an inner surface, wherein the inner surface generally attaches to one or more actuators of an animatronic device by attachment links. In one embodiment, the outer surface of the surface geometry is configured to closely match at least one of the target surfaces from step 602. For example, the outer surface may be configured to match a "neutral" expressive pose from one of the surfaces. In one embodiment, the inner surface may be based on one or more thickness parameters representing a thickness distribution of the surface geometry. The thickness parameters comprise one or more parameters indicating a material thickness of a synthetic skin at a given point in the skin's geometry. The thickness parameters may comprise a variable distribution of thickness indicating a varied inner surface of the skin geometry that may enable certain shapes of the outer surface when the synthetic skin is deformed. In one embodiment, at step 604, the thickness parameters may be initialized to a default value, such as a parameter representing a uniform thickness.

According to one embodiment, a thickness direction for the skin geometry may be determined using the 3D geometry previously acquired. In one embodiment, a low-pass filtered version of the skin's outer surface may be computed and utilized to construct a parameterization $r: \mathfrak{R}^2 \to \mathfrak{R}^3$ using a uv-mapping technique, for example such as found in conventional uv-mapping software. In one embodiment, a roughly area-preserving map may be generated for obtaining unbiased sample distributions.

Figure 7A:
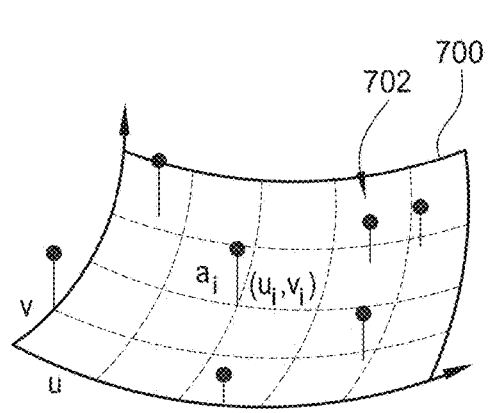
FIGS. 7A-B are conceptual illustrations of parameterization of a geometric surface, according to one embodiment of the invention.
Figure 7B:
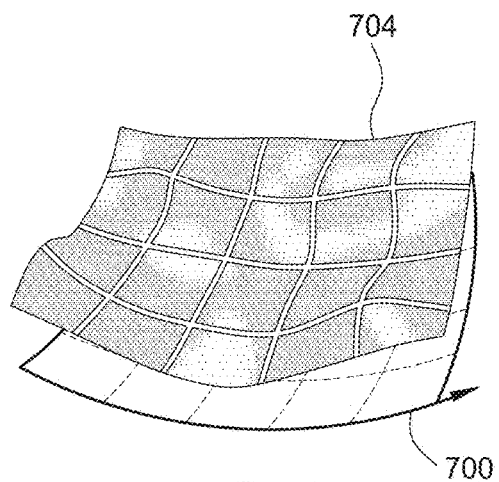

FIGS. 7A-B are conceptual illustrations of parameterization of a geometric surface 700, according to one embodiment of the invention. As shown in FIG. 7A, the geometric surface 700 may be parameterized to represent an undeformed state of the synthetic skin. In one embodiment, the undeformed geometry of skin may be described as $X=r(u,v)+hn(u,v)$, where u and v are surface coordinates and a thickness parameter h runs along the surface's normal direction n.

According to one embodiment, rather than working directly with undeformed positions, a warping heightfield may be defined on the surface 700 in order to smoothly deform space along its normal direction. According to one embodiment, a smooth warping field may comprise a plurality of height samples 702 generated using a moving least squares (MLS) interpolation. As shown in the embodiment depicted in FIG. 7A, the smooth warping field w(u,v) may be constructed from a sparse set of height samples a, at positions $(u_i, v_i)^T$ using the MLS interpolation. FIG. 7B illustrates an MLS warping field 704 shown as a surface with isoparametric lines for clarity of illustration. In one embodiment, the resolution of the warping heightfield may be controlled by adaptively placing the locations of the height samples 702 in u-v space. In one embodiment, the locations of height samples 702 may be based on a user-provided density map.

Figure 8:
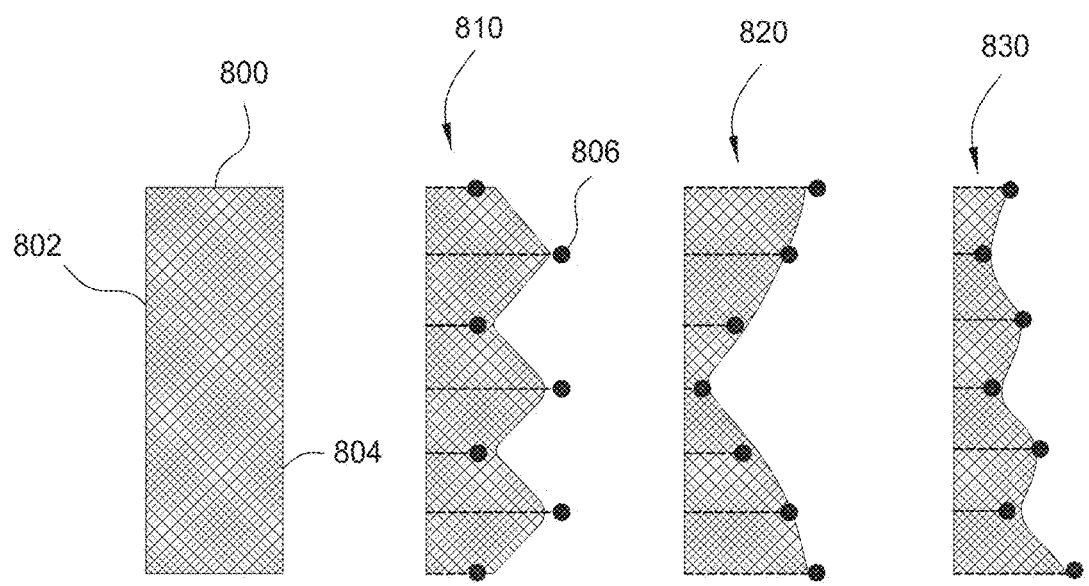
FIG. 8 is a conceptual illustration of surface iterations, according to one embodiment of the invention.

FIG. 8 is a conceptual illustration of surface iterations, according to one embodiment of the invention. In one embodiment, a simple on-dimensional example wherein shape variations may be generated according to the parameterization of the undeformed state of the synthetic skin. As shown, an input geometry 800 may comprise an outer surface 802 and an inner surface 804. In one embodiment, warped geometries 810, 820, and 830 may be generated by varying the inner surface 804, e.g., by varying values of the height samples 806 distributed over the u-v space.

According to one embodiment, the MLS warping field 704 may be evaluated at an arbitrary parameter point (u, v) by fitting an affine transformation that minimizes the weighted least square error, provided by:

$$\sum_i \theta(\|(u, v)^T - (u_i, v_i)^T\|) \|a(u, v)^T (1, u_i, v_i) - \alpha_i\|^2, \tag{7}$$

where θ(x) may be a weighting kernel and $a(u,v)^T \in \mathfrak{R}^3$ are the local coefficients of the interpolation function. The latter may be determined by solving the normal equations for Equation 7, for example, using pre-computation. According to one embodiment, the parameterized undeformed geometry of the synthetic skin may now be optimized as described in detail below.

Returning to FIG. 6, at step 606, the processor optimizes the plurality of thickness parameters using a computational model simulating a deformed state of the surface geometry when actuated to best match the target surfaces. The computational model may be determined using an optimization technique adapted to minimize an elastic energy with respect to rest state positions of the synthetic skin. In one embodiment, a dedicated parameterization approach using a moving least squares (MLS) interpolation technique may be utilized to modify and optimize the skin shape only in its thickness direction (e.g., thickness parameter).

Embodiments of the invention provide a generic optimization framework that may be applied to various types of parameters relating to physical face cloning. In one embodiment, a function $\hat{W}(\hat{x},p)$ may be determined that denotes the total energy of a physical system (e.g., the animatronic device), including internal deformation energies and external contributions to the potential. The parameter p may represent a vector of generic parameters to be optimized. The parameter $\hat{x}$ may contain a subset of the deformed positions x of the physical simulation. All other values of x may be either constant (i.e., constrained) or computable from p. In one embodiment, both the undeformed and deformed positions of a simulated mesh may be allowed to depend on p, as follows:

$$\hat{W}(\hat{x},p) = W(x(\hat{x},p), X(p)) + W_{ext}(x(\hat{x},p)). \tag{8}$$

In one embodiment, for fixed parameter values p, the physical system may assume an equilibrium state, as shown by Equation 8:

$$\hat{x}_{eq}(p) = \underset{\hat{x}}{\operatorname{argmin}}(\hat{W}(\hat{x}, p)) \tag{9}$$

that minimizes the total energy of the system, leading to a condition of a vanishing residual force:

$$\left. \frac{\partial \hat{W}}{\partial \hat{x}} \right|_{\hat{x}_{eq},(p)} = 0. \tag{10}$$

In one embodiment, the aim of the optimization framework is to find optimal parameter values p such that the positions $\hat{x}(\hat{x}_{eq}, p), p)$ match a desired target configuration as closely as possible. The match "proximity" may be measured in terms of a matching energy $E_{match}(x)$. In one embodiment, the parameters may be regularized using a regularization energy $E_{reg}(p)$.

Accordingly, the optimization framework may be solved as a minimization problem with respect to $\hat{x}$ and p, with an objective function seen in Equation 11:

$$E(\hat{x}, p) = \frac{1}{2}\gamma \left\| \frac{\partial \hat{W}}{\partial \hat{x}} \right|_{\hat{x},p} \right\|^2 + E_{match}(x(\hat{x}, p)) + E_{reg}(p), \tag{11}$$

wherein the first term penalizes a violation of the condition seen in Equation 10, ensuring with a sufficiently high penalty γ that the resulting $\hat{x}$ is close to a physical solution with vanishing residual forces.

According to embodiments of the invention, a matching energy function may be utilized to measure how well a configuration of surface positions x is in agreement with a target surface. In one embodiment, a set of points may be embedded in the simulation domain and may be deformed according to the mapping φ described above. In one implementation, a subset of points from a high-resolution 3D scans described above may be utilized. Due to the choice of basis functions, the deformed position of a point may be computed as a linear combination of four nodal positions. The matching energy may then be computed as a squared distance between the deformed points and their desired target positions q (i.e., desired positions in the target surfaces), $$E_{match}(x) = \frac{1}{2}\|Sx - q\|^2, \tag{12}$$

where the matrix S comprise weights for the computation of the deformed points from x.

According to embodiments of the invention, the minimization problem, as seen in Equation 11, may be solved and/or computed using one or more suitable computational approaches. In one implementation, Equation 11 may be numerically optimized using a Newton method. As such, first and second derivatives are computed with respect to $\hat{x}$ and p. In one embodiment, the second derivatives of the first term in Equation 11 may be computed only approximately, ignoring the third order derivatives of W that may result from applying the chain rule. In each Newton step, a sparse direct solver may be utilized to solve the linear system:

$$H\begin{pmatrix} \Delta\hat{x} \\ \Delta p \end{pmatrix} = -f \tag{13}$$

for increments $\Delta\hat{x}$ and $\Delta p$, where f is the vector of first derivatives of E and H contains its second derivatives. In one embodiment, a line search approach may be utilized to ensure the energy decreases in each Newton step. In one embodiment, the condition where the matrix H becomes indefinite may be detected by the direct solver by not being able to factorize H, in which case additional techniques may be utilized, such as adding a multiple of the identity to H.

According to one embodiment, the optimization process may be utilized to modify a local thickness of the synthetic skin geometry in such a way that when mechanical actuators of the animatronic device are set to values corresponding to a particular expressive pose, the resulting deformation of the skin matches the expressive poses' target positions q as closely as possible. In a physical simulation, the actuators settings result in hard positional constraints that can be directly be applied to the corresponding deformed positions. Parameters $p_{thk}$ may be determined that indicate a thickness distribution in an undeformed configuration without directly affecting the deformed positions of the synthetic skin. In one embodiment, the parameters $p_{thk}$ may be determined using Equation 11, described above, and Equation 14, as follows:

$$\hat{W}(\hat{x}, p_{thk}) = W(\hat{x}, X(p_{thk})) \pm W_{ext}(\hat{x}). \tag{14}$$

where Equation 11 may be minimized to find the parameter values for the thickness distribution that best matches a given target surface.

In one embodiment, the thickness distribution may be represented by a parameterized surface, such as described in FIGS. 7A-B above. In one embodiment, the parameters $\alpha_i$ of all sample points, as described above, may be gathered into $p_{thk}$, and optimal height values may be computed by minimizing Equation 11. It is noted that the MLS interpolation described in FIGS. 7A-B result in a linear mapping between undeformed positions X and parameters $p_{thk}$, thus the matrix $\partial X / \partial p_{thk}$ may be constant and, consequently, may be pre-computed.

After the optimal $\alpha_i$ values have been computed, a final rest configuration may be computed as follows. According to one embodiment, for each $X_a$ of the original mesh, its parameter values $(u_a, v_a, h_a)$ may be retrieved, the MLS warping field may be evaluated to obtain $w_a = w(u_a, v_a)$ and then compute the warped positions as $X'_a = r(u_a, v_a) + w_a h_a n(u_a, v_a)$.

According to one embodiment, the undeformed mesh with nodal positions $X(p_{thk})$ may be validated as a tetrahedral mesh where every element has a positive volume utilizing any suitable techniques. In one embodiment, the deformation energy function W may be re-used, such that $X(p_{thk})$ is deemed as the deformed configuration and the initial undeformed positions $X(1)$ as the undeformed configuration:

$$E_{reg}(p_{thk}) = \gamma_{undefreg} W(X(p_{thk}), X(1)) \qquad (15)$$

For any positive penalty value $\gamma_{undefreg}$, this energy may tend to infinity as any element's volume approaches zero, effectively preventing element inversions in the undeformed configuration. Additionally, according to one embodiment, a quadratic energy term may be added to $E_{reg}$ that penalizes MLS weights exceeding a value of one, thereby preventing a thickness of the skin from increasing.

Embodiments of the invention may also provide for optimization of the skin geometry for the multiple expressive poses comprising the target surfaces. The undeformed configuration $X(p_{thk})$ may be optimized such that a plurality of poses (i.e., m>1) may be reproduced as closely as possible. In one embodiment, for a set of actuator settings $a_i$, the given target positions $q_i$ may be matched as closely possible. In one implementation, the optimization process described may be modified such that optimization is performed for all deformed positions $\hat{x}_1, \ldots, \hat{x}_m$ and $p_{thk}$ at once. The m matching functions $E_{match_1}^i$ and the objective function may be re-written as:

$$E(\hat{x}, p_{thk}) = \sum_{i=1}^{m} \frac{1}{2} \gamma \left\| \frac{\partial \hat{W}}{\partial \hat{x}} \bigg|_{\hat{x}_i, p_{thk}} \right\|^2 \qquad (16)$$

$$+ \sum_{i=1}^{m} E_{match}^i(x(\hat{x}_i, p_{thk})) \qquad (17)$$

$$+ E_{reg}(p_{thk}) \qquad (18)$$

According to one embodiment, the optimization may be initialized with values $\hat{x}_i$ computed from a per-pose forward simulation with increased loading, and may utilize $p_{thk}=1$ for the MLS parameters.

The method 600 continues at step 608, where the processor generates a plurality of actuation parameters, where each actuation parameter is optimized to deform the surface geometry such that deformed surface base matches a corresponding one of the target surfaces. The actuation parameter optimization according to embodiments of the invention find the best values for controlling the mechanical actuators of the animatronic device such that the resulting deformed skin matches a given target pose as closely as possible. In one embodiment, parameters $p_{act}$ of the optimization may be defined positional constraints to apply to the nodal positions x. Accordingly, in the objective function (i.e., the optimization framework) shown above in Equation 11, the following energy function may be utilized:

$$\hat{W}(\hat{x}, p_{act}) = W(x(\hat{x}, p_{act}), X) + W_{ext}(x(\hat{x}, p_{act})) \qquad (19)$$

In one embodiment, the mapping from unconstrained nodal positions $\hat{x}$ and parameters $p_{act}$ to deformed positions x may be provided as follows:

$$x_i \begin{cases} \hat{x}_i & \text{if node } i \text{ unconstrained} \\ M_a(p_{act}) X_i & \text{if node } i \text{ constrained by actuator } a \end{cases} \qquad (20)$$

For clarity, the transformation matrix $M_a(p_{act})$ of actuator a may be linearized around the current parameter values $p_{act}$ in each step of the optimization. According to one embodiment, similar to the thickness optimization, the regularization energy function $E_{reg}$ may be utilized to keep the actuator parameter values within the range of physically feasible values (i.e., operational range of the motorized actuators).

Animatronic Head

Embodiments of the invention provide an animatronic head configured to actuate a synthetic skin fabricated according the techniques described above. While a synthetic skin fabricated according to the optimization process is discussed in conjunction with one embodiment of the animatronic head, it is understood that any controlling mechanism configured to deform the synthetic skin is within the scope of embodiments of the invention.

The animatronic head may comprise a head-shaped body having a plurality of electromechanical actuators disposed thereon. In one embodiment, the actuators may be driven by electric motors. In another embodiment, the electromechanical actuators may be shape memory alloy (SMA) actuators. In one embodiment, a synthetic skin may be retained on the animatronic head and coupled to the plurality of actuators via one or more attachment links (i.e., moving links). As such, the actuators may be distributed across the surface of the head-shaped body and are configured to actuate so as deform the synthetic skin as described herein. In one embodiment, the animatronic head further comprises a plurality of rigid attachment links that constrain the movement of the skin. In one particular implementation, the animatronic head features a=13 parameters $p_{act} \in \Re^a$ to control the movement of I=17 attachment links.

In one embodiment, the operating range and control parameters of the animatronic head may be determined by attaching a marker to each moving link. Locations and orientations of each link may be sampled such a similar capture system as discussed above for the face scanning step during the acquisition phase. In one embodiment, a mapping $m(P_{act}) \in \Re^a \to \Re^{I \cdot 3 \cdot 2}$ from animation parameters $p_{act}$ to the 3D locations and orientations of the attachment points may then be specified by quadratically interpolating the samples. These are then used as hard boundary constraint in our forward simulation. To obtain the specific animation parameters for a given facial expression, an inverse problem may be solved as described in step 608 above.

While embodiments of the invention describe a framework where the attachment of the actuators is fixed under specific places underneath the synthetic skin, it is contemplated that embodiments of the invention may be extended to relax this constraint and provide additional degrees of freedom in optimizing the synthetic skin geometry. In one embodiment, the rest shape of the synthetic skin may not be the same as the rest shape of the underlying animatronic device.

Fabrication

Embodiments of the invention provide for fabrication of a synthetic skin having a surface geometry generated and optimized as described above. According to embodiments of the invention, the synthetic skin may be comprised of an elastically deformable polymer material having high yield strength. In one embodiment, the synthetic skin may be fabricated from silicone, due to the fact that the stiffness of silicone may be controlled accurately, its color may be adjusted, is robust, and the fabrication process is relatively save and requires little special equipment. While embodiments of the invention discuss the synthetic comprising a single material such as silicone, it is contemplated that certain aspects of the invention may be extended to fabricate a synthetic skin using a multi-layered variable material so as to extend the range of possible deformation capable by the skin.

In one embodiment, a liquid injection molding technique may be applied to fabricate the synthetic skin. Silicone may be injected into a 3D mold using a pressure gun. In one embodiment, a 3D mold comprises a core having an impression corresponding to the inner surface of the synthetic skin, as optimized above, and a plurality of outer parts. According to one embodiment, the 3D mold may comprise six outer parts configured to be disassembled such that the skin may be removed from the 3D mold without destroying the mold. In one embodiment, the mold may be fabricated using suitable manufacturing means, particularly a rapid manufacturing process such as a rapid prototyping 3D printing. In one implementation, a two part silicone rubber, available as GI-245 from Silicones, Inc., may be utilized with varying amounts of plasticizer. After mixing the silicone with the corresponding catalyst, the silicone comprises a silicone consistency which may then be injected into the mold described above. Approximately seven days of room temperature curing may be required until the synthetic skin is ready to be used.

Validation

Embodiments of the invention provide techniques for validating the processing pipeline discussed herein. In one embodiment, the computational model simulating the deformation behavior of the synthetic skin material, as determined based on the acquisition phase comprising measuring, modeling, and simulating silicone materials, may be validated. In one embodiment, a comparison may be made between a force-strain curve of a simulated material (i.e., according to the computational model) and a force-strain curve of a measured sample. In one implementation, a sample may be measured using a uni-axial stretch and compression test on a rectangular (e.g., 55×5×2 mm, for stretch) and cylindrical (e.g., 50 mm diameter, 12 mm height, for compression) object. Additionally, the behavior of three simulated bars for bending and under gravity as predicted by the computational model may be compared to the real-world behavior of three bars made of different silicone materials.

Embodiments of the invention also provide techniques for validating the optimization process, as discussed, wherein a volumetric shape of soft-tissue material may be computed such that the surface matches the deformation of a given target surfaces under actuation. In one embodiment, the optimization process may be validated in simulation. "Ground truth data" may be generated by randomly varying the thickness of a uniform block using the moving least squares (MLS) warp to generate a plurality of test objects as described above. A plurality of test target surfaces may then be extracted from the forward simulation of these objects. Then, the test target surfaces and the uniform (i.e., undeformed) block may be fed as input into the optimization process described above. It has been determined through experimentation that the techniques described herein are able to exactly reproduce the spatially-varying thickness of the "ground truth" objects that were used to generate the input target surfaces.

In one embodiment, a subset of these "ground truth" objects may be fabricated, and deformed under a test environment to compare the deformation of the predicted optimized shape to the real object. It was has been determined that for 95 mm long bars, the average shape errors between the deformed fabricated shape and the goal shape are 0.44 mm (top) and 0.38 mm (bottom).

Embodiments of the invention further provide techniques for validating the entire processing pipeline by physically cloning (i.e., fabricating) a human face for an animatronic figure. In one example, an expressive performance for a test subject may be captured and acquired (e.g., more than 100 frames). A neutral pose from the captured performance may be selected and aligned to a scan of the animatronic head. It was noted that in some cases the animatronic head may have pronounced cheek bone structures, in which case the acquired 3D geometry of the test subject's face may be warped slightly to prevent intersections.

In one embodiment, the gap between the surface of the neutral pose and the underlying animatronics may define an initial un-optimized skin. In one implementation, the initial un-optimized skin may be represented as a tetrahedral mesh comprising approximately 27 thousand elements. In one embodiment, to better represent important facial deformation features on the forehead, an additional high-resolution mesh comprising 64 thousand elements may be added to optimize this area. The optimization process according to embodiments of the invention may then be utilized to first obtain animation parameters for the entire captured face performance. For matching criteria, small regions may be selected, such as small local regions close to the skin attachment links. In those regions, the surface thickness is constrained and may not be changed because the synthetic skin is connected to the moving and/or static link. However, for all other regions, the optimization process as described may be utilized to achieve a desired deformation behavior by varying the skin thickness. In one experiment, a reduced subset of four expressive poses for thickness optimization was used. A comparison may be generated between the deformed shape made using the un-optimized volumetric shape and the optimized volumetric shape. Additionally, the optimized volumetric shape may be used to fabricate a real test object. In one example, an optimized skin may be fabricated using material with Young's modulus of E=78000 and Poisson's ratio of v=0.47 in its cured state. As such, the fabricated skin may be retained on the animatronic head as provided above and may be compared to the human test face (as well as the simulation) under various facial expressions.

Embodiments of the invention provide a process for computationally-guided design of an animatronic character composed of a soft-tissue material and an electromechanical base. In one embodiment, a volumetric shape of the soft-tissue material and a set of actuation forces are computed that can reproduce target deformations of an exterior character surface. As an example, this process allows for the construction of an animatronic head that replicates the shape and behavior of a real person whose expressions are acquired using a 3D scanning system. The core element of this process is a physically-based simulation framework that allows for accurate prediction of the behavior of the soft tissue material when subject to external forces (e.g., actuation forces). According to the experimental validation techniques described above, this process permits the design of a soft-tissue animatronic character that accurately mimics a given real person.

One advantage of embodiments of the invention is the ability to produce realistic animatronic characters using an automatic computational-based design pipeline that reduces manual and labor-intensive iterations from conventional design approaches. Another advantage of embodiments of the invention includes an enhanced realism of specific expressive poses of the human subject.

Various embodiments of the invention may be implemented as a program product for use with a computer system. The program(s) of the program product define functions of the embodiments (including the methods described herein) and can be contained on a variety of computer-readable storage media. Illustrative computer-readable storage media include, but are not limited to: (i) non-writable storage media (e.g., read-only memory devices within a computer such as CD-ROM disks readable by a CD-ROM drive, flash memory, ROM chips or any type of solid-state non-volatile semiconductor memory) on which information is permanently stored; and (ii) writable storage media (e.g., floppy disks within a diskette drive or hard-disk drive or any type of solid-state random-access semiconductor memory) on which alterable information is stored.

One or more embodiments of the invention have been described above with reference to specific details to provide a more thorough understanding of embodiments of the invention. Persons skilled in the art, however, will understand that various modifications and changes may be made thereto without departing from the broader spirit and scope of embodiments of the invention. The foregoing description and drawings are, accordingly, to be regarded in an illustrative rather than a restrictive sense.

What is claimed is:

1. A method for generating an object shape for a synthetic skin, the method comprising:
determining a first target surface and a second target surface, wherein the first target surface comprises a neutral target pose, and the second target surface comprises an expressive target pose;
generating a shape geometry for the synthetic skin, the shape geometry having an outer surface and an inner surface, wherein the outer surface is determined based on the first target surface comprising the neutral target pose;
generating one or more material parameters for the synthetic skin based on a computational model that simulates deformation behavior of a fabricated object having the shape geometry and made from a defined physical material, such that the outer surface of the shape geometry in a deformed state more closely matches the expressive target pose of the second target surface; and
fabricating the synthetic skin based on the shape geometry and the one or more material parameters, wherein the one or more material parameters define physical attributes of the synthetic skin.

2. The method of claim 1, further comprising:
determining one or more actuator parameters associated with the second target surface for controlling a corresponding mechanical actuator configured to deform the synthetic skin, wherein the actuator parameters are selected to deform the shape geometry in a manner such that the outer surface of the deformed shape geometry matches the second target surface.

3. The method of claim 1, further comprising:
generating the computational model based on one or more material parameters of a material, wherein the computational model is configured to simulate deformation behavior of an object fabricated from the material.

4. The method of claim 1, further comprising:
capturing stress-strain behavior of a sample comprised of a material; and
determining one or more material parameters based on an objective function minimized to approximate the captured stress-strain behavior; and
generating the computational model based on the one or more material parameters.

5. The method of claim 1, further comprising:
determining an operational range of an animatronic device comprising a plurality of attachment paths; and
modifying the computational model by utilizing the determined operational range as boundary constraint for forward simulation.

6. The method of claim 1, wherein modifying the inner surface comprises:
determining an energy minimization function based on the computational model, wherein the computational model comprises a neo-Hookean material model configured to simulate a deformed state of the shape geometry based on a plurality of material parameters; and
modifying the shape geometry based on the energy minimization function.

7. The method of claim 1, wherein modifying the inner surface comprises:
determining how closely the outer surface of the shape geometry in the deformed state matches the second target surface according to an objective function comprising a matching energy function representing a level of conformity of an input surface to the second target surface.

8. The method of claim 1, wherein the shape geometry further comprises one or more object parameters that represent a property selected from a group consisting of material distribution, thickness, density, and stiffness.

9. A non-transitory computer-readable storage medium containing computer program code, that, when executed, performs an operation to generate an object shape for a synthetic skin, the operation comprising:
determining a first target surface and a second target surface, wherein the first target surface comprises a neutral target pose, and the second target surface comprises an expressive target pose;

generating a shape geometry having an outer surface and an inner surface, wherein the outer surface is determined based on the first target surface comprising the neutral target pose;

generating one or more material parameters for the synthetic skin based on a computational model that simulates deformation behavior of a fabricated object having the shape geometry and made from a defined physical material, such that the outer surface of the shape geometry in a deformed state more closely matches the expressive target pose of the second target surface; and fabricating the synthetic skin based on the shape geometry and the one or more material parameters, wherein the one or more material parameters define physical attributes of the synthetic skin.

10. The non-transitory computer-readable storage medium of claim 9, wherein the operation further comprises:

determining one or more actuator parameters associated with the second target surface for controlling a corresponding mechanical actuator configured to deform the synthetic skin, wherein the actuator parameters are selected to deform the shape geometry in a manner such that the outer surface of the deformed shape geometry matches the second target surface.

11. The non-transitory computer-readable storage medium of claim 9, wherein the operation further comprises:

generating the computational model based on one or more material parameters of a material, wherein the computational model is configured to simulate deformation behavior of an object fabricated from the material.

12. The non-transitory computer-readable storage medium of claim 9, wherein the operation further comprises:

capturing stress-strain behavior of a sample comprised of a material; and determining one or more material parameters based on an objective function minimized to approximate the captured stress-strain behavior; and generating the computational model based on the one or more material parameters.

13. The non-transitory computer-readable storage medium of claim 9, wherein the operation further comprises:

determining an operational range of an animatronic device comprising a plurality of attachment paths; and modifying the computational model by utilizing the determined operational range as boundary constraint for forward simulation.

14. The non-transitory computer-readable storage medium of claim 9, wherein the operation comprising modifying the inner surface further comprises:

determining an energy minimization function based on the computational model, wherein the computational model comprises a neo-Hookean material model configured to simulate a deformed state of the shape geometry based on a plurality of material parameters; and modifying the shape geometry based on the energy minimization function.

15. The non-transitory computer-readable storage medium of claim 9, wherein the operation comprising modifying the inner surface further comprises:

determining how closely the outer surface of the shape geometry in the deformed state matches the second target surface according to an objective function comprising a matching energy function representing a level of conformity of an input surface to the second target surface.

16. The non-transitory computer-readable storage medium of claim 9, wherein the shape geometry further comprises one or more object parameters that represent a property selected from a group consisting of material distribution, thickness, density, and stiffness.

17. A system to generate an object shape for a synthetic skin, the system comprising:

one or more computer processors; and a memory containing a program which when executed by the processors performs an operation comprising:

determining a first target surface and a second target surface, wherein the first target surface comprises a neutral target pose, and the second target surface comprises an expressive target pose;

generating a shape geometry having an outer surface and an inner surface, wherein the outer surface is determined based on the first target surface comprising the neutral target pose;

generating one or more material parameters for the synthetic skin based on a computational model that simulates deformation behavior of a fabricated object having the shape geometry and made from a defined physical material, such that the outer surface of the shape geometry in a deformed state more closely matches the expressive target pose of the second target surface; and fabricating the synthetic skin based on the shape geometry and the one or more material parameters, wherein the one or more material parameters define physical attributes of the synthetic skin.

18. The system of claim 17, wherein the operation further comprises:

determining one or more actuator parameters associated with the second target surface for controlling a corresponding mechanical actuator configured to deform the synthetic skin, wherein the actuator parameters are selected to deform the shape geometry in a manner such that the outer surface of the deformed shape geometry matches the second target surface.

19. The system of claim 17, wherein the operation further comprises:

generating the computational model based on one or more material parameters of a material, wherein the computational model is configured to simulate deformation behavior of an object fabricated from the material.

20. The system of claim 17, wherein the operation further comprises:

determining an operational range of an animatronic device comprising a plurality of attachment paths; and modifying the computational model by utilizing the determined operational range as boundary constraint for forward simulation.

* * * * *

UNITED STATES PATENT AND TRADEMARK OFFICE
CERTIFICATE OF CORRECTION

PATENT NO. : 10,403,404 B2
APPLICATION NO. : 14/797755
DATED : September 3, 2019
INVENTOR(S) : Bernd Bickel et al.

Page 1 of 1

It is certified that error appears in the above-identified patent and that said Letters Patent is hereby corrected as shown below:

In the Specification

In Column 12, Line 39, delete "a," and insert -- $\alpha_i$ --, therefor.

In Column 14, Line 61, delete " $\hat{W}(\hat{x}, p_{thk}) = W(\hat{x}, X(p_{thk})) \pm W_{ext}(\hat{x}).$ "
and insert -- $\hat{W}(\hat{\mathbf{x}}, \mathbf{p}_{thk}) = W(\hat{\mathbf{x}}, \mathbf{X}(\mathbf{p}_{thk})) + W_{ext}(\hat{\mathbf{x}}).$ --, therefor.

In Column 16, Line 58, delete " $m(P_{act}) \in \mathfrak{R}^a \to \mathfrak{R}^{1 \cdot 3 \cdot 2}$ "
and insert -- $m(\mathbf{p}_{act}) \in \mathfrak{R}^a \to \mathfrak{R}^{l \cdot 3 \cdot 2}$ --, therefor.

Signed and Sealed this
Thirty-first Day of December, 2019

Andrei Iancu
*Director of the United States Patent and Trademark Office*